(12) United States Patent
Sato

(10) Patent No.: US 6,623,683 B2
(45) Date of Patent: Sep. 23, 2003

(54) METHOD FOR PRODUCING HUMAN BODY PART PROSTHESIS

(75) Inventor: Masahiro Sato, Uji (JP)

(73) Assignee: Sato Giken Co., Ltd., Kyoto (JP)

( * ) Notice: Subject to any disclaimer, the term of this patent is extended or adjusted under 35 U.S.C. 154(b) by 19 days.

(21) Appl. No.: 09/977,446

(22) Filed: Oct. 15, 2001

(65) Prior Publication Data

US 2002/0175444 A1 Nov. 28, 2002

(30) Foreign Application Priority Data

May 25, 2001 (JP) .................................... 2001-156322

(51) Int. Cl.[7] ............................................. B29C 33/40
(52) U.S. Cl. ...................................... 264/222; 264/227
(58) Field of Search ................................. 264/222, 227

(56) References Cited

U.S. PATENT DOCUMENTS

| | | | | |
|---|---|---|---|---|
| 2,473,723 A | * | 6/1949 | Nelson | 264/222 |
| 2,580,264 A | * | 12/1951 | Wright et al. | 264/222 |
| 3,811,133 A | * | 5/1974 | Harris | 264/222 |
| 4,272,878 A | * | 6/1981 | Danforth | 264/222 |
| 4,401,492 A | * | 8/1983 | Pfrommer | 264/222 |
| 4,600,551 A | * | 7/1986 | Erb | 264/222 |
| 5,035,758 A | * | 7/1991 | Degler et al. | 156/61 |
| 5,527,359 A | * | 6/1996 | Nakamura et al. | 623/7 |
| 5,798,062 A | * | 8/1998 | Thielbar | 264/40.1 |
| 6,136,027 A | * | 10/2000 | Jackson | 623/7 |

\* cited by examiner

Primary Examiner—Allan R. Kuhns
(74) Attorney, Agent, or Firm—Kirschstein, et al.

(57) ABSTRACT

A method for producing a human body part prosthesis, in the case where one pattern of human body part is lost or removed from a generally symmetrical human body part consisting of the left pattern and the right pattern, for restoring the lost or removed human body part, the method comprising: a reverse molding step in which a form of the remaining human body part $B_L$ of the other pattern is impression modeled directly from the remaining human body part of the other pattern, and an impression model of one pattern which is lost or removed is reverse-molded from the impression model 10 of the other pattern thus impression modeled, and a prosthesis molding step for molding a human body part prosthesis 1 of the lost or removed side from the reversed impression model 18 molded in the reverse molding step.

4 Claims, 7 Drawing Sheets

A

B

C

METHOD FOR PRODUCING HUMAN BODY PART PROSTHESIS

TECHNICAL FIELD

The present invention relates to a method for producing a human body part prosthesis which, in the case where one pattern of human body part is lost or removed from a generally symmetrical human body part consisting of the left pattern and the right pattern, restores the human body part which is lost or removed and, in particular, the present invention provides an artificial breast of the type that is used with not being implanted into a human body but being attached to a patient in association with body shaping of the patient whose breast has been removed by a surgical operation for breast cancer and the like. The present invention is widely applicable as a human body part prosthesis for body shaping of a patient whose body part is lost because of a traffic accident, other injury accidents and the like without limited to the case of the artificial breast as described above.

BACKGROUND ART

As is well known in the art, for example, with regard to reformation of breast part of a patient whose whole or part of breast has been removed by a surgical operation for breast cancer and the like, there are two measures: plastic surgical operation such as breast reconstituting operation and the like; and attaching of an artificial breast. The former measure of plastic surgical operation requires skilled techniques and has a lot of problems in terms of safety, reliability and appearance, or in terms of economics because the cost of such plastic surgical operation is expensive, and moreover it is almost impossible to recover the original shape. As a result of this, the latter measure of artificial breast is commonly used.

Conventional artificial breasts are provided not as a reproduction of the breast of a patient herself, but merely as a ready-made one which is produced based on a typical pattern. Breast in human body largely varies among individuals in terms of shape, size, color, texture and the like, so that it should principally be custom-made as an artificial breast having a shape adapted to the shape of the individual patient. In particular, in the case of the breast cancer and the like, the probability that the cancer develops in both sides of mammary gland tissue is low, and it is often the case that only one side breast is removed because of the cancer.

In view of the above, according to the present invention, in the case where one of breasts is removed by an operation for breast cancer and the like and the other of breasts remains, the remaining breast is directly impressed, and a negative model obtained based on the impression is reversed, thereby providing a base for molding a breast of the removed side. According to such a configuration, in contrast to conventional ready-made artificial breasts, it is possible to provide an artificial breast of a symmetrical shape that reproduces various forms such as shape, size, color, texture and the like on the basis of the remaining breast of the patient herself. This could offer a mental relief to the patient who unfortunately has lost a part of her body and suffers severe pain, since the lost part of her body is revived by utilizing reversal of the remaining part of her own body.

DISCLOSURE OF THE INVENTION

To be more specific, for achieving the above-described object, the present invention provides a method for producing a human body part prosthesis, in the case where one pattern of human body part is lost or removed from a generally symmetrical human body part consisting of the left pattern and the right pattern, for restoring the lost or removed human body part, the method comprising:

a reverse molding step in which a form of the remaining human body part of the other pattern is impression modeled directly from the remaining human body part of the other pattern, and an impression model of one pattern which is lost or removed is reverse-molded from the impression model of the other pattern thus impression modeled, and a prosthesis molding step for molding a human body part prosthesis of the lost or removed side from the reversed impression model molded in the reverse molding step.

Furthermore, the present invention provides a method for producing a human body part prosthesis, wherein the generally symmetrical human body part consisting of the left pattern and the right pattern is generally symmetrical breasts.

Furthermore, the present invention provides a method for producing a human body part prosthesis, wherein the generally symmetrical human body part consisting of the left pattern and the right pattern is generally symmetrical cheeks, ears, hips, or the like generally symmetrical limbs.

Furthermore, the present invention provides a method for producing a human body part prosthesis, in the case where one pattern of human body part is lost or removed from a generally symmetrical human body part consisting of the left pattern and the right pattern, for restoring the lost or removed human body part, the method comprising:

the first step of making a negative silicone model by impression modeling the form of the remaining human body part of the other pattern directly from the remaining human body part of the other pattern;

the second step of making a positive plaster model from the negative silicone model;

the third step of making a negative silicone model for reversal from the positive plaster model;

the fourth step of reversing the negative silicone model for reversal and making a mother model from the reversed negative silicone model for reversal;

the fifth step of making a mold (negative plaster model) from the mother model; and the sixth step of making a prosthesis from the mold (negative plaster model).

In the following, a method for producing a human body part prosthesis which forms the present invention will be described in detail on the basis of concrete examples shown in drawings in which the method is applied to production of an artificial breast.

BRIEF DESCRIPTION OF THE DRAWINGS

FIG. 1 show a concrete example of an artificial breast produced by the present invention, in which FIG. 1A is a schematic perspective view of the artificial breast, FIG. 1B is a schematic sectional side elevation showing the cross section along the vertical direction, FIG. 1C is a schematic section view showing the cross section along the horizontal direction, FIG. 1D is a schematic section view showing the state that the artificial breast is attached to an affected part of the human body, viewed in the downward direction from the head.

FIG. 2 show the process until the step of making a negative silicone model, in which FIG. 2A is a schematic section view of a patient herself having a remaining breast portion and a breast removed portion after breast removal, viewed in the downward direction from the head, FIG. 2B is a schematic section view showing the state that impression modeling is conducted by applying an impression agent on the remaining breast portion and the breast removed portion of the patient, and FIG. 2C is a schematic section view of a negative silicone model obtained after completion of the impression modeling.

FIG. 3 show the process of making a positive plaster model from the negative silicone model, in which FIG. 3A is a schematic section view of the negative silicone model (same as FIG. 2C), FIG. 3B is a schematic section view showing the sate that plaster is poured into the negative silicone model, and FIG. 3C is a schematic section view of a positive plaster model obtained after completion of the modeling using the plaster (artificial human body model).

FIG. 4 show the process of making a negative silicone model for reversal from the positive plaster model, in which FIG. 4A is a schematic section view of the positive plaster model (same as FIG. 3C), FIG. 4B is a schematic section view showing the state that impression is conducted by applying silicone on the remaining breast portion in the positive plaster model, FIG. 4C is a schematic section view of a negative silicone model for reversal obtained after completion of the impression modeling from the positive plaster model, and FIG. 4D is a schematic section view showing the state that the negative silicone model for reversal is reversed (the state that the inner surface of the impression modeling is turned to outside).

FIG. 5 show the process of making a mother model from the reversed negative silicone model for reversal, in which FIG. 5A is a schematic section view of the reversed negative silicone model for reversal (same as FIG. 4D), FIG. 5B is a schematic section view showing the state that plaster is poured into the negative silicone model for reversal, FIG. 5C is a schematic section view of a mother model obtained after completion of plaster filling, FIG. 5D is a schematic section view showing the state of making a mold (negative plaster model) from the mother model, and FIG. 5E is a schematic section view of a mold (negative plaster model) obtained after completion of modeling by the mother model.

FIG. 6 show the process of molding an artificial breast main body from the mold (negative plaster model) and forming an artificial breast by the artificial breast main body and an affected part attaching molded member, in which FIG. 6A is a schematic section view (same as FIG. 5F) of the mold (negative plaster model), FIG. 6B is a schematic section view showing the state that impression molding in the mold (negative plaster model) is conducted using a molding material for artificial breast main body, FIG. 6C is a schematic section view of an artificial breast main body obtained after completion of impression modeling from the mold (negative plaster model), FIG. 6D is a schematic section view showing the state that the interior of the artificial breast main body is appropriately filled with a filler, FIG. 6E is a schematic section view showing the state that an affected part attaching molded member is attached to the artificial breast main body after filling with the filler, and FIG. 6F is a schematic section view showing a completed artificial breast.

FIG. 7 show the process of conducting impression modeling of an affected part attaching molded member in artificial breast from the removed side of the positive plaster model (artificial human body model), in which FIG. 7A is a schematic section view of the positive plaster model (same as FIG. 4A), FIG. 7B is a schematic section view showing the state that impression modeling of the removed side is conducted by using the affected part attaching mold material, and FIG. 7C is a schematic section view showing the affected part attaching molded member obtained after completion of the modeling using the positive plaster model.

BEST MODE FOR EMBODYING THE INVENTION

Figure 1:
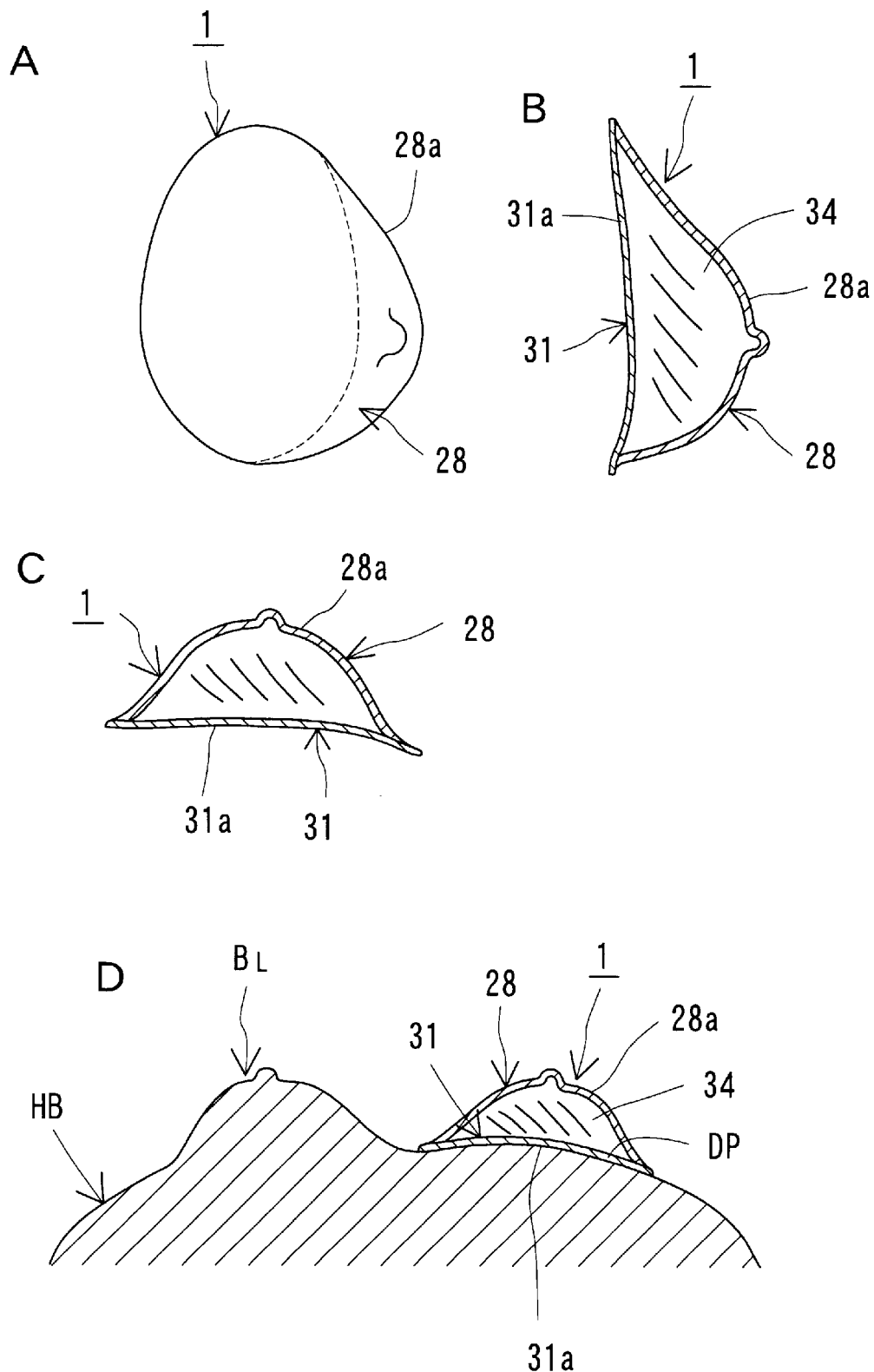
Figure 2:
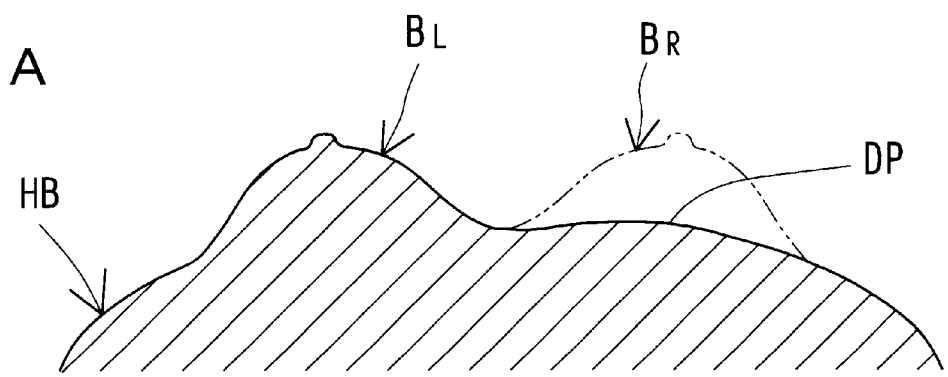
FIGS. 2 to 7 are views for sequentially explaining the production process with respect to the method for producing an artificial breast which forms the present invention.
Figure 2:
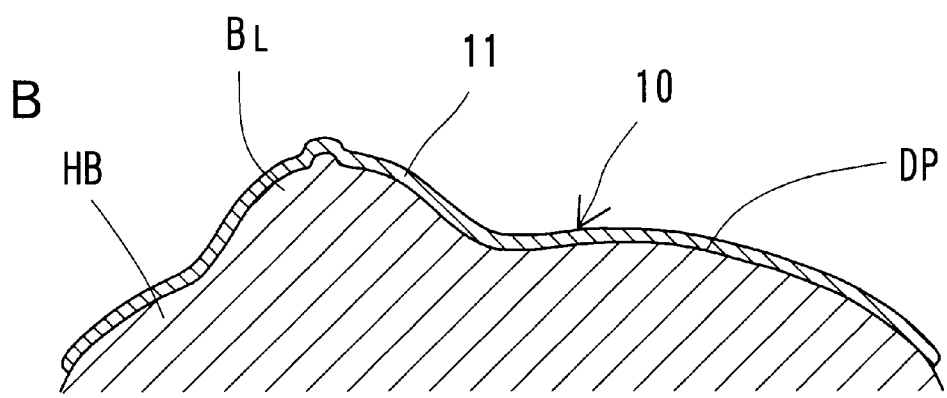
Figure 2:
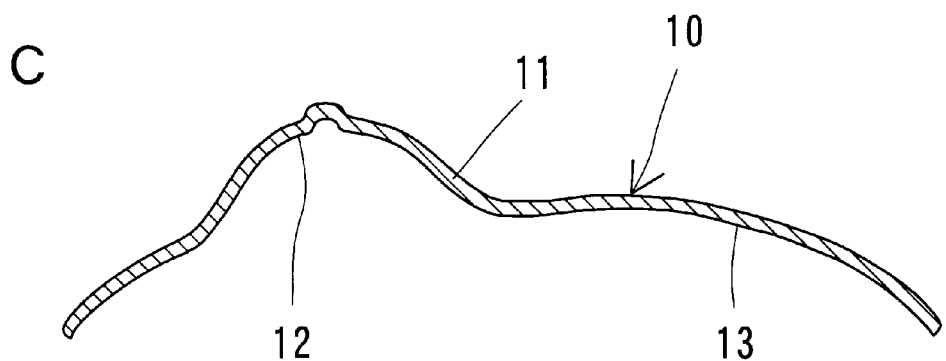
Figure 3:
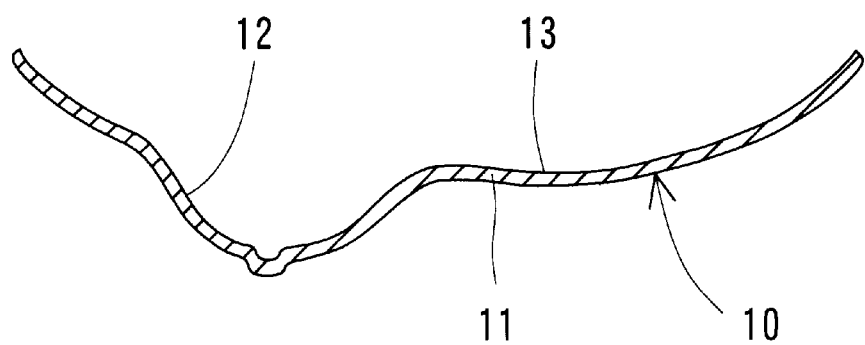
Figure 3:
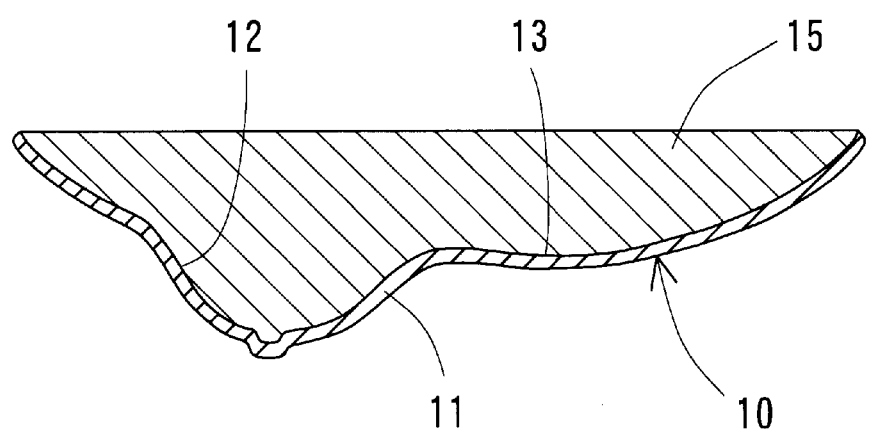
Figure 3:
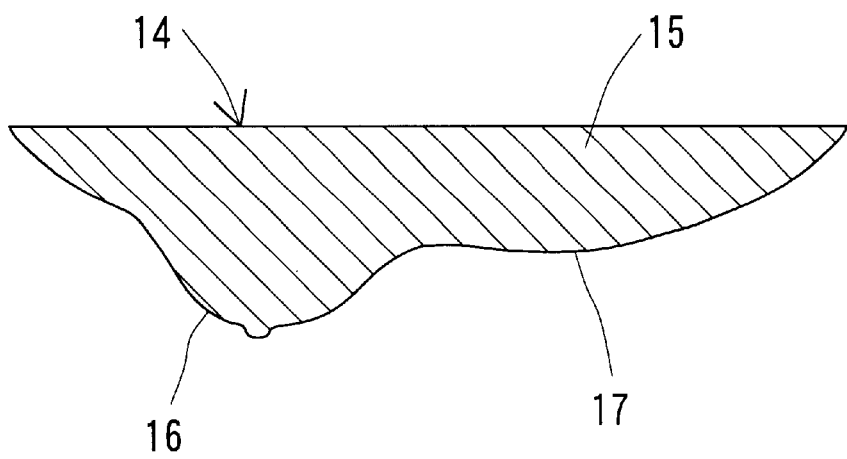
Figure 4:
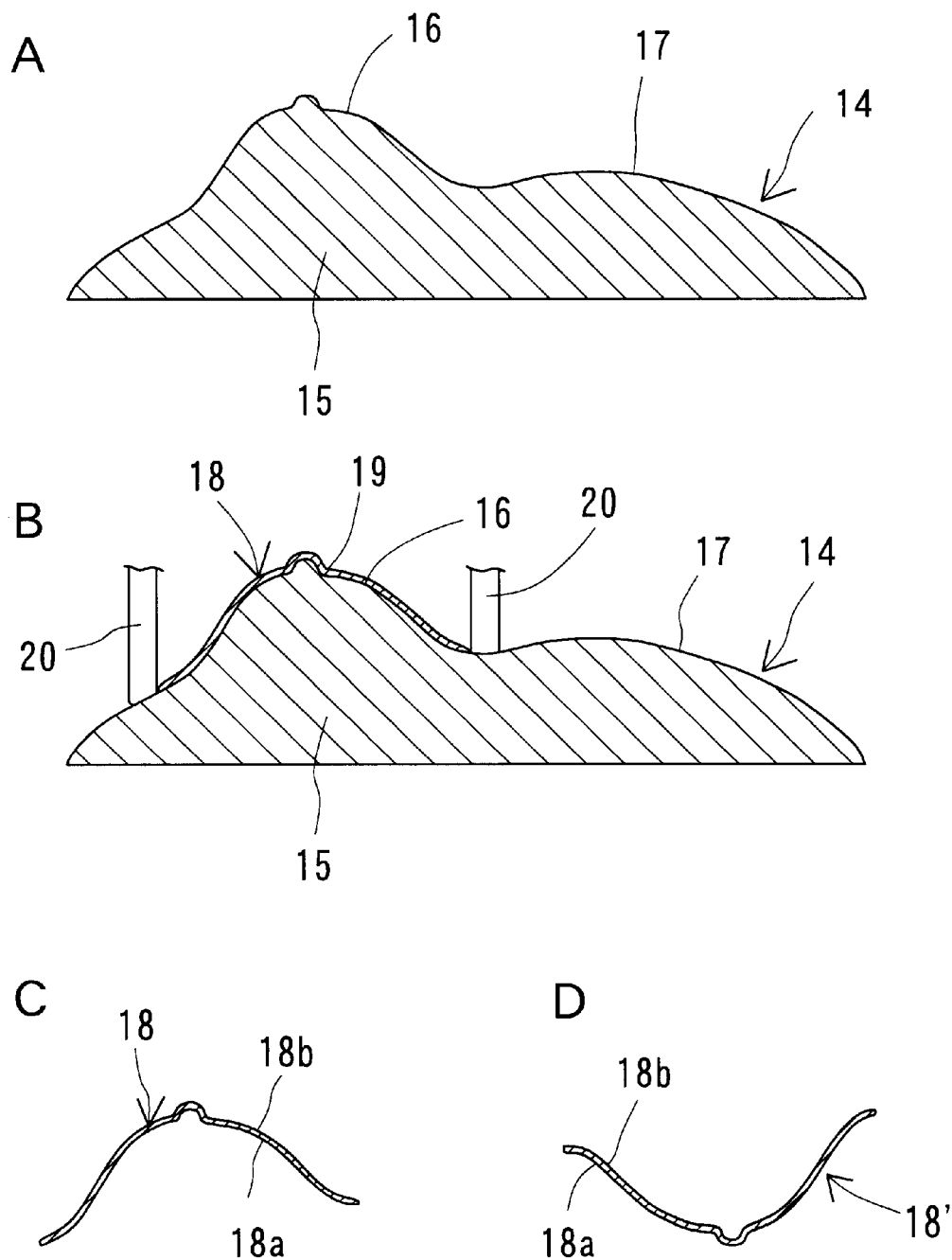
Figure 5:
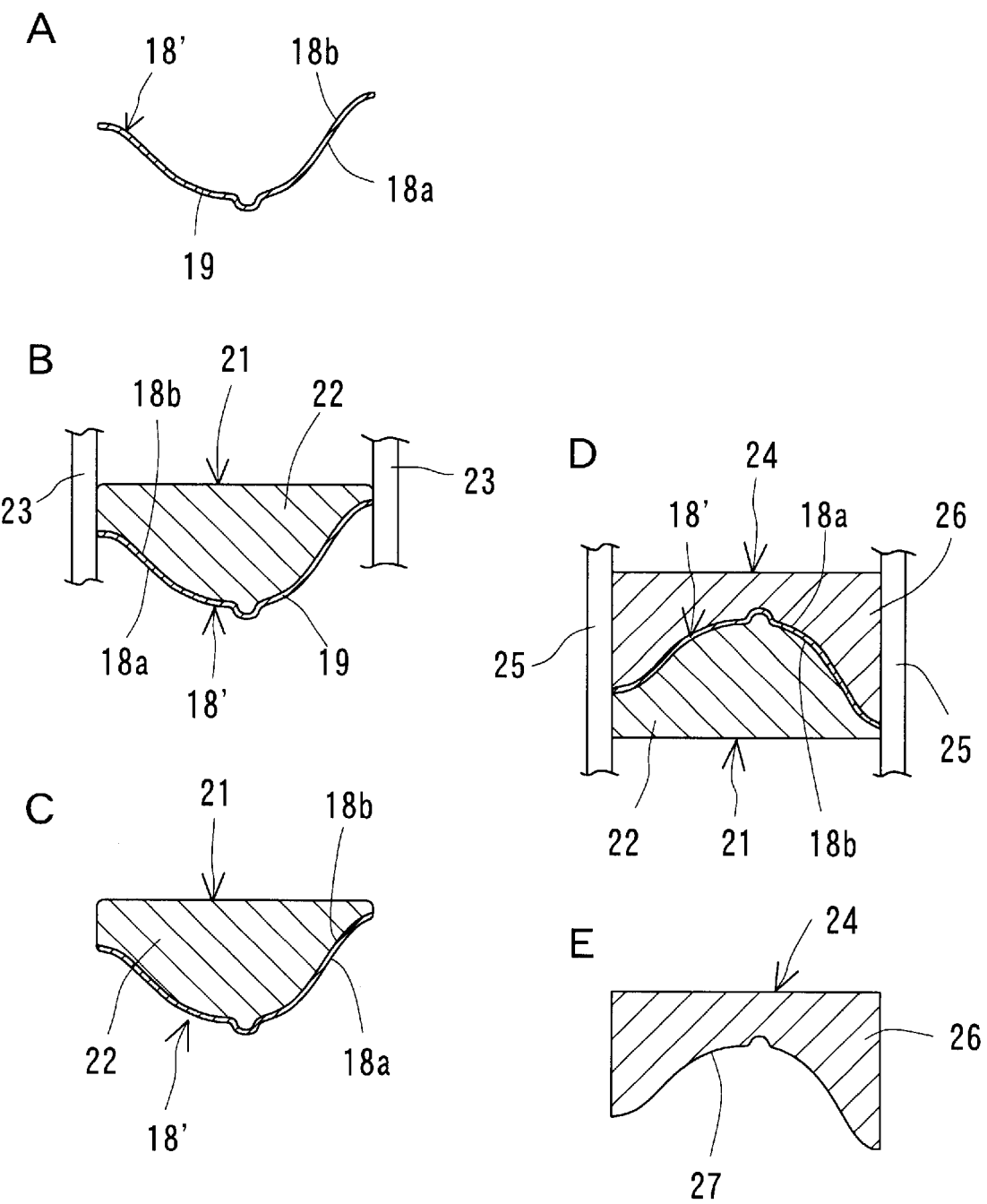
Figure 6:
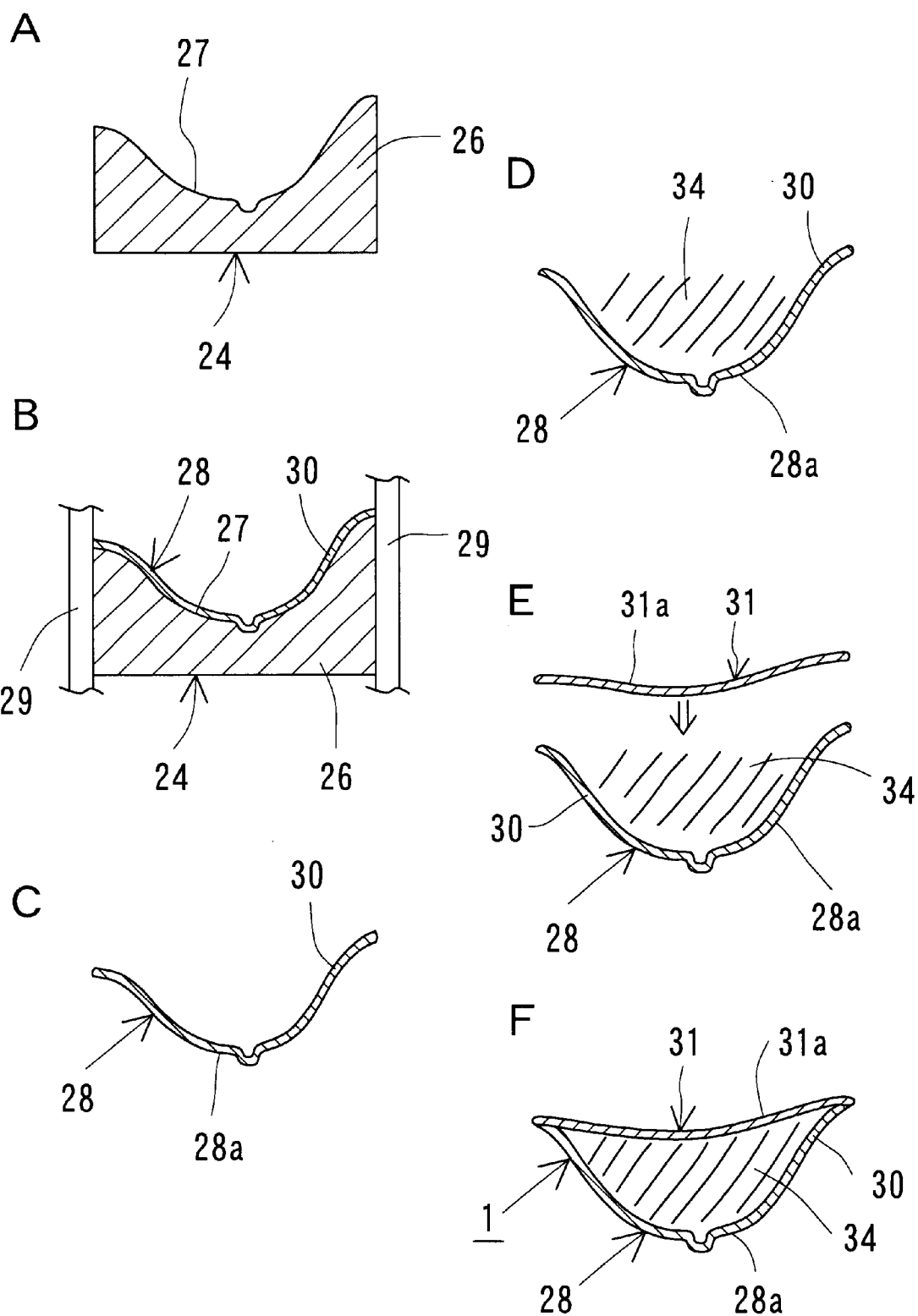

First, referring to FIGS. 2 to 7, a method for producing a human body part prosthesis which forms the present invention will be explained in detail based on the concrete examples in which the method is applied to production of an artificial breast. In the concrete examples shown in drawings, the human body of the patient is denoted by the reference symbol "HB", and for example, in the clinical case where the right pattern of breast is removed, the remaining breast is denoted by the reference symbol "BL" and the removed breast is denoted by the reference symbol "BR". Then the affected part after removal is denoted by the reference symbol "DP".

1. First step: step of making a negative silicone model 10 (see FIG. 2).

In the first step, the remaining breast BL of the left pattern and the affected part DP after removal of the removed breast BR of the right pattern are directly impression modeled by means of an impression modeling agent 11, to thereby make a negative silicone model 10. The impression modeling agent used in the first step is a silicone impression agent or an alginic acid impression agent. The negative silicone model 10 comprises a left pattern breast negative model portion 12 resulting from impression modeling of the remaining breast BL of the left pattern, and a removed affected part negative model portion 13 resulting from impression modeling of the affected part DP after removal. FIG. 2C is a section view of the negative silicone model 10 completed by this first step.

In the present invention, since the first step includes direct contact with a patient, special care must be taken in the following points. First of all, it is preferred that the impression modeling from the patient body HB in the first step is conducted in the standing or sitting position. In this case, as the impression modeling agent, materials of relatively low fluidity should be selected in consideration of the law of gravitation. However, if skilled technique of conducting the modeling directly before hardening is available, such a special consideration about viscosity of the impression modeling agent is not necessary. In this first step, in preparation for unexpected happenings, the impression modeling should be duplicated as a precaution for preparing two types of negative models, and additionally materials for confirming the shape, proportion, color and the like of the remaining breast BL in the patient body HB should be recorded by photographing, video recording and the like.

In one example, the impression modeling agent in this first step is a silicone impression agent and is prepared in an amount of 200 g to 500 g depending on the body shape of the patient. The silicone impression agent thus prepared will harden, for example, in about 8 minutes under the environment of room temperature of 20C. The impression modeling operation in this first step is achieved by applying and overlaying the impression modeling agent to the human body HB of the patient to be impression molded so that the thickness is about 5 to 15 mm.

2. Second step: step of making a positive plaster model 14 from the negative silicone model 10 (see FIG. 3).

This second step, in which plaster 15 is poured into the negative silicone model 10 made in the first step (see FIG. 3B), thereby making a positive plaster model 14 to be an artificial human body model, requires accurate modeling from the negative silicone model 10. The positive plaster model 14 comprises a left pattern breast positive model portion 16 resulting from impression modeling of the left pattern breast negative model portion 12 in the negative silicone model 10, and a removed affected part positive model portion 17 resulting from impression modeling of the removed affected part negative model portion 13 in the negative silicone model 10.

FIG. 3C is a section view of the positive plaster model 14 completed by this second step.

3. Third step: step of making a negative silicone model for reversal 18 from the positive plaster model 14 (see FIG. 4).

In this third step, a silicone impression agent 19 for modeling is poured into the positive plaster model 14 made in the second step (see FIG. 4B), to thereby make a negative silicone model for reversal 18. This third step intends to reproduce the removed right pattern breast BR from the remaining left pattern breast BL of the patient, and the right pattern breast BR is reproduced by reversing the impression model of the remaining left pattern breast BL. Therefore, in the third step, the negative model should be made into a layer of minimum thickness so far as the shape as a model can be maintained, considering in advance the reversing step for making the negative silicone model for reversal 18. This negative silicone model for reversal 18 comprises an inner surface of left pattern breast negative model 18a which is modeled in direct contact with the left pattern breast positive model portion 16 in the positive plaster model 14, and an outer surface of left pattern breast negative model 18b. FIG. 4C is a section view showing the negative silicone model for reversal 18 completed by the third step, FIG. 4D is a section view showing the state that the negative silicone model for reversal 18 is turned inside out so that the inner surface of left pattern breast negative model 18a is the outer surface.

The third step is the most important step in the present invention. In the third step, first a frame 20 is assembled for the unnecessary part in the positive plaster model 14 in advance, and the silicone impression agent 19 for modeling is poured into the inside of the frame 20. This frame 20 is useful in the point that it is possible to omit the subsequent cutting operation of the unnecessary part of the negative silicone model for reversal 18, to save the impression agent, and to mold the surrounding portion of the negative silicone model for reversal 18 thicker.

According to a more preferred example, in the third step, a mold release agent such as mold releasing soapsuds, silicone mold release agent, Vaseline or the like is applied on the modeling surface of the positive plaster model 14, and after allowing the mold release agent to dry, the silicone impression agent 19 for modeling is applied. This silicone impression agent 19 for modeling is, for example, about 100 g of TOSHIBA silicone mixed with 0.5% of a hardening agent. The silicone impression agent 19 for modeling thus formulated will harden in about 8 minutes under the environment of room temperature of 20C. It is preferred that the layer thickness of the silicone impression agent 19 for modeling is about 0.2 mm to 0.5 mm in the peripheral part of the papilla including the areola of nipple, and about 1.5 mm to 3.0 mm in the lower part of the breast.

4. Fourth step: step of reversing the negative silicone model for reversal and making a mother model 21 from the reversed negative silicone model for reversal 18' (see FIGS. 5A to 5C).

In this fourth step, with respect to a negative silicone model for reversal 18' in the reversed state that is obtained by turning the negative silicone model for reversal 18 made in the third step inside out, a frame 23 is provided and plaster 22 and the like is filled, to thereby make a mother model 21 (see FIG. 5B). The mother model 21 consists of the reversed negative silicone model for reversal 18' and the plaster 22, as shown in FIG. 5C, and is provided as an integrated positive model in the step of making a mold (negative plaster model) described below.

5. Fifth step: step of making a mold (negative plaster model) 24 from the mother model 21 (see FIGS. 5D to 5E).

In this fifth step, with respect to the mother model 21 made in the fourth step, a frame 25 is provided and plaster 26 is filled, thereby making a mold (negative plaster model) 24 (see FIG. 5D). This mold (negative plaster model) 24 comprises a mold surface 27 which is modeled in correspondence with the outer surface 18a of the negative silicone model for reversal 18' in the mother model 21.

The plaster 26 for this mold (negative plaster model) 24 may be common dental plaster, or may be plaster in which dental plaster and plaster containing a reinforcing resin are mixed in the ratio of 3:1 for the purpose of improving the strength.

6. Sixth step: step of making an artificial breast main body 28 from the mold (negative plaster model) 24 and making an artificial breast 1 from the artificial breast main body 28 and an affected part attaching molded member 31 as described below (see FIGS. 6A to 6F).

In this sixth step, with respect to the mold (negative plaster model) 24 made in the fifth step, a frame 29 is provided, a molding material for artificial breast main body 30 is poured, thereby making an artificial breast main body 28 (see FIG. 6B). This artificial breast main body 28 comprises an artificial breast main body surface 28a which is modeled in correspondence with the mold surface 27 in the mold (negative plaster model) 24. The molding material for artificial breast main body 30 is silicone mixed with a color material for realizing the color in the periphery of the affected part recorded from the patient in the first step.

Figure 7:
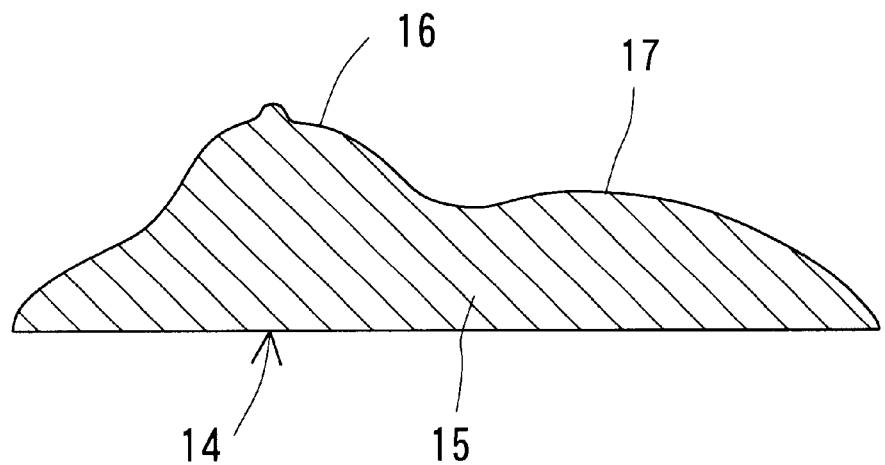
Figure 7:
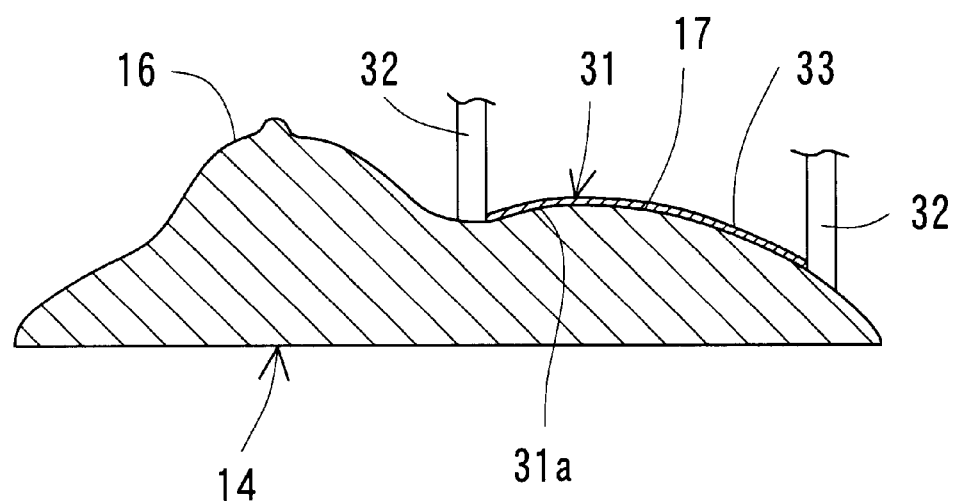
Figure 7:
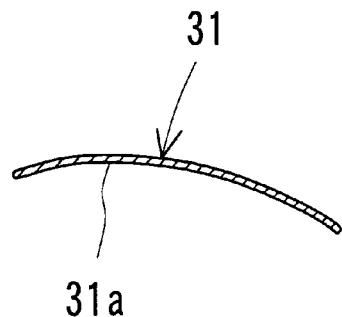

On the other hand, as shown in FIG. 7, the affected part attaching molded member 31 is molded by impression molding from the removed affected part positive model portion 17 in the positive plaster model 14 using the positive plaster model 14 made from the negative silicone model 10 in the second step as a model. That is, the affected part attaching molded member 31 is made by providing a frame 32 and applying a molding material for affected part attaching 33, with respect to the removed affected part positive model portion 17 in the positive plaster model 14 made in the second step. This affected part attaching molded member 31 comprises an affected part attaching surface 31a in correspondence with the removed affected part positive model portion 17 in the positive plaster model 14.

In the sixth step, the artificial breast 1 is made from the artificial breast main body 28 made from the mold (negative plaster model) 24 and the affected part attaching molded member 31 impression modeled from the removed affected part positive model portion 17 in the positive plaster model 14. The process of making the artificial breast 1 is achieved, as shown in FIGS. 6D to 6F, by filling the interior of the artificial breast main body 28 made from the mold (negative plaster model) 24 with a desired filler 34 such as urethane foam (the interior may be hollow without using the filler), and adhering the molding material for affected part attaching 31 on the backside of the artificial breast main body 28 filled with the filler 34.

The artificial breast 1 according to one concrete example of the present invention exhibits the forms shown in FIGS. 1A to 1C, and can be used with being attached to the removed affected part DP removed by a surgical operation of breast cancer and the like with the used of adhesives and the like as shown in FIG. 1D.

It is to be noted that the present invention is not limited to the artificial breast explained above as a concrete example. That is, the present invention can also be applied to generally symmetrical human body part consisting of the left pattern and the right pattern, or generally symmetrical cheeks, ears, hips or the like generally symmetrical limbs as a human body part prosthesis without any modification, for instance, in the case where such part is removed because of an accident or pathological reason.

According to the present invention having the above-described configuration, the artificial breast 1 made as one concrete example of the invention comprises the artificial breast main body 28 which is made based on the right pattern model that is made by reversing the left pattern model on the basis of the left pattern model impression modeled directly from, for example, the left pattern remaining breast BL of the patient herself who has her one breast removed by a surgical operation for breast cancer, and the affected part attaching molded member 31 obtained by impression modeling directly from the removed affected part of the removed breast side, the artificial breast 1 providing an artificial breast inherent to the patient herself, and offering an excellent prosthesis that will not cause any abnormal feelings in attached to the affected part, so that significant advantage is obtained in that points.

What is claimed is:

1. A method of producing a prosthesis to replace a missing human body part from an available human body part that is bilaterally symmetrical to the missing part, the method comprising the steps of:

a) making a negative model by direct impression modeling of the available part;

b) making a positive model from the negative model;

c) making a negative reversal model from the positive model;

d) reversing the negative reversal model to make a mother model;

e) making a mold from the mother model; and f) making the prosthesis from the mold.

2. The method of claim 1, wherein the prosthesis is shaped as a human breast.

3. The method of claim 1, wherein the steps a) and c) are each performed by using silicone.

4. The method of claim 1, wherein the steps b) and e) are each performed by using plaster.

* * * * *